(12) United States Patent
Coats et al.

(10) Patent No.: US 10,918,808 B2
(45) Date of Patent: Feb. 16, 2021

(54) ANGLED INJECTION NOZZLE

(71) Applicant: Portal Instruments, Inc., Cambridge, MA (US)

(72) Inventors: Andrew Coats, Somerville, MA (US); Robert J. Dyer, Concord, MA (US)

(73) Assignee: Portal Instruments, Inc., Cambridge, MA (US)

(*) Notice: Subject to any disclaimer, the term of this patent is extended or adjusted under 35 U.S.C. 154(b) by 819 days.

(21) Appl. No.: 15/454,426

(22) Filed: Mar. 9, 2017

(65) Prior Publication Data
US 2017/0259012 A1 Sep. 14, 2017

Related U.S. Application Data

(60) Provisional application No. 62/305,688, filed on Mar. 9, 2016.

(51) Int. Cl.
*A61M 5/34* (2006.01)
*A61M 5/31* (2006.01)
*A61M 5/28* (2006.01)

(52) U.S. Cl.
CPC .............. *A61M 5/345* (2013.01); *A61M 5/28* (2013.01); *A61M 5/3134* (2013.01); *A61M 2005/342* (2013.01)

(58) Field of Classification Search
CPC ...... A61M 5/30; A61M 5/3007; A61M 5/345; A61M 5/28; A61M 5/3134; A61M 2005/341; A61M 2005/342; A61M 2005/2433; A61M 2005/2485; A61M 2005/24; A61M 5/24; A61M 5/2422
See application file for complete search history.

(56) References Cited

U.S. PATENT DOCUMENTS

| | | | | |
|---|---|---|---|---|
| 2,688,968 A * | 9/1954 | Scherer | .................. | A61M 5/30 604/72 |
| 3,140,713 A * | 7/1964 | Ismach | .................. | A61M 5/30 604/68 |
| 3,788,315 A | 1/1974 | Laurens | | |
| 5,074,843 A * | 12/1991 | Dalto | ...................... | A61M 5/30 604/68 |
| 5,730,723 A * | 3/1998 | Castellano | .............. | A61M 5/30 604/143 |
| 5,927,562 A * | 7/1999 | Hammen | ................ | A61M 5/28 222/327 |

(Continued)

FOREIGN PATENT DOCUMENTS

| | | |
|---|---|---|
| DE | 20105183 U1 | 6/2002 |
| DE | 10146535 A1 | 4/2003 |
| WO | 2006/086719 A1 | 8/2006 |

*Primary Examiner* — Shefali D Patel
*Assistant Examiner* — Tezita Z Watts
(74) *Attorney, Agent, or Firm* — Occhiuti & Rohlicek LLP

(57) ABSTRACT

An adapter for use with an injection device includes a first end, a second end and a first longitudinal axis extending from the first end and the second end. The adapter also includes a chamber defined by a sidewall between the first end and second end and a nozzle having a passageway extending through the sidewall, the passageway having an input at the chamber, an output at an outer surface of the body and a passageway axis extending from the input to the output, the passageway axis being angularly offset from the longitudinal axis of the channel. A cartridge can include such an adapter.

19 Claims, 5 Drawing Sheets

(56) References Cited

U.S. PATENT DOCUMENTS

| | | |
|---|---|---|
| 2002/0055729 A1 | 5/2002 | Goll |
| 2002/0095124 A1 | 7/2002 | Palasis et al. |
| 2005/0194472 A1* | 9/2005 | Geser ................. B05B 15/18 |
| | | 239/602 |
| 2008/0009788 A1* | 1/2008 | Hunter ............... A61M 5/3007 |
| | | 604/68 |
| 2011/0186167 A1* | 8/2011 | Lee ...................... G01N 15/00 |
| | | 138/37 |
| 2015/0246183 A1* | 9/2015 | Kavokin ............... A61M 5/30 |
| | | 604/506 |

* cited by examiner

ANGLED INJECTION NOZZLE

CROSS REFERENCE TO RELATED APPLICATIONS

This application claims priority to U.S. Provisional Application No. 62/305,688, filed on Mar. 9, 2016, the contents of which are hereby incorporated by reference in their entirety.

BACKGROUND

This invention relates to administering an injectate to a target underlying a contact surface with a needle-free injector.

The skin of organisms such as humans serves as a protective barrier that, among other functions, prevents pathogens from entering the body and prevents or regulates fluids such as blood and water from exiting the body. In the field of modern medicine, there is often a need to deliver injectates such as drugs through the skin and into the bloodstream of patients. Traditionally, this delivery of liquids into a patient's body is accomplished by insertion of a needle through the patient's skin and into an area inside of the patient's body where the liquid can enter the patient's blood stream.

However, the use of needles to deliver liquids into a patient's body has a number of significant drawbacks such as the pain associated with being pierced by a needle, the fear that many patients have of needles, and the skin damage and associated risk of infection that occurs due to the use of needles.

As a result, needle-free transdermal injection devices have been developed. These devices use a high pressure, narrow jet of injection liquid or powder to penetrate a patient's skin, obviating the need to pierce the patient's skin with a needle.

In the drug delivery space, each therapeutic has a designated injection route that is dependent on such factors as the timescale of the drug action, the dosage frequency, the required absorption rate for intended effect, and the target location(s), among others. The subcutaneous (SC) space, in particular, is a target for many needle-free drug delivery devices, as the SC route is considered to be useful for a number of applications and indications. When injecting into the SC space, ensuring that the injectate does not pass through the SC layer and into deeper layers is highly desirable. Injectate penetration beyond the SC space may reduce treatment efficacy, cause patient discomfort or pain, and/or damage internal tissues or organs. Hence, needle-free devices may be designed with the intent that the injectate reaches and does not pass beyond the subcutaneous layer. However, there is a non-zero risk that the injectate may go beyond the subcutaneous layer into the muscle or deeper tissue. The relative risk of unintended injectate penetration is largely dependent on the specific devices' underlying mechanisms.

SUMMARY

In a general aspect of the invention, an adapter for use with an injection device includes a first end, a second end and a first longitudinal axis extending from the first end and the second end, a chamber defined by a sidewall between the first end and second end, and a nozzle having a passageway extending through the sidewall, the passageway having an input at the chamber, an output at an outer surface of the body and a passageway axis extending from the input to the output, the passageway axis being angularly offset from the longitudinal axis of the channel.

In another aspect of the invention, a cartridge administers an injectate to a target underlying a contact surface. The cartridge has a distal end and comprises a housing having an axis extending from a proximal end to a distal end of the housing, the housing having a bore extending along a first longitudinal axis from the proximal end to the distal end and an opening at the distal end of the housing and an adapter disposed at the distal end of the housing. The adapter includes a body having a first end, a second end and a second longitudinal axis extending from the first end and the second end and substantially in parallel with the first longitudinal axis; a chamber defined by a sidewall between the first end and second end, and a nozzle having a passageway extending through the sidewall, the passageway having an input at the chamber, an output at an outer surface of the body and a passageway axis extending from the input to the output, the passageway axis being angularly offset from the first longitudinal axis of the channel.

Embodiments of these aspects may include one or more of the following features.

The passageway includes a taper, over a path length from a first dimension (e.g., a first diameter) at the input of the nozzle to a second dimension (e.g., a second diameter), less than the first dimension at the output of the nozzle. The path length of the taper is at least about 0.5 mm in length (preferably 1.0 mm), and the taper of the passageway defines a shape, in a plane that includes the passageway axis, that is a continuous and monotonically decreasing function of distance along the passageway axis in a direction of flow through the nozzle. The passageway has a cross-sectional area, and the taper of the passageway causes the cross-sectional area, as a function of distance along the longitudinal axis in the direction of flow, to decrease in a manner such that a first derivative of the function is negative, continuous, and monotonically increasing, and wherein a second derivative of this function is always positive along the path length. The shape of the taper has a non-zero second derivative over the path length and can be approximately exponential. The first derivative of the shape of the taper has an approximately constant value over a portion of the taper. The taper is shaped to provide a ratio of (1) radial velocity of material at the output of the nozzle to (2) axial velocity of material at the output of the nozzle, which is less than about 0.50. A diameter at the output of the nozzle is less than about 300 μm. preferably less than about 200 μm, and more preferably less than about 100 μm.

The cartridge may include an injection head disposed at the distal end of the housing. The injection head may include a skin depressor for deforming the contact surface such that the contact surface is substantially perpendicular to the passageway axis. The injection head may include a channel extending along the passageway axis from an opening in the distal end of the bore to an injection opening of the injection head. The channel may include a first portion with a cuboid shape and a second, open portion. The channel may have a cylindrical shape. The channel may have an arched shape. The cartridge may include a plunger disposed in the bore for ejection of injectate from the bore.

Among other advantages, an adapter having the above features as well as a cartridge that includes the adapter increases the likelihood that the injectate is delivered into the subcutaneous layer and not into surrounding tissue layers, such as the dermis and muscle layers. Furthermore, because injector users are accustomed to positioning the injector substantially perpendicular or normal to the surface of the skin, the cartridge and adapter allow the injectate to be delivered through the skin at a non perpendicular angle when the injector is substantially perpendicular to the skin. Thus, depth of penetration by the narrow jet of injectate can be controlled by directing the narrow jet into the skin at a non-perpendicular angle to the skin while allowing the user to position the injector relative to the skin in a repeatable and familiar manner.

Moreover, when the cartridge includes a skin depressor, the outer surface of the depressor grips the contact surface (i.e., skin) of the subject so that the injectate passing through the nozzle is injected through the epidermis and dermis and into the subcutaneous space. Gripping the contact surface stabilizes and maintains the position of the cartridge and prevents it from rocking from side to side. That is, in the event of relative movement (e.g., due to movement of the subject), the target remains fixed relative to the cartridge.

Other features and advantages of the invention are apparent from the following description, and from the claims.

DESCRIPTION

Cartridge Overview

Figure 1:
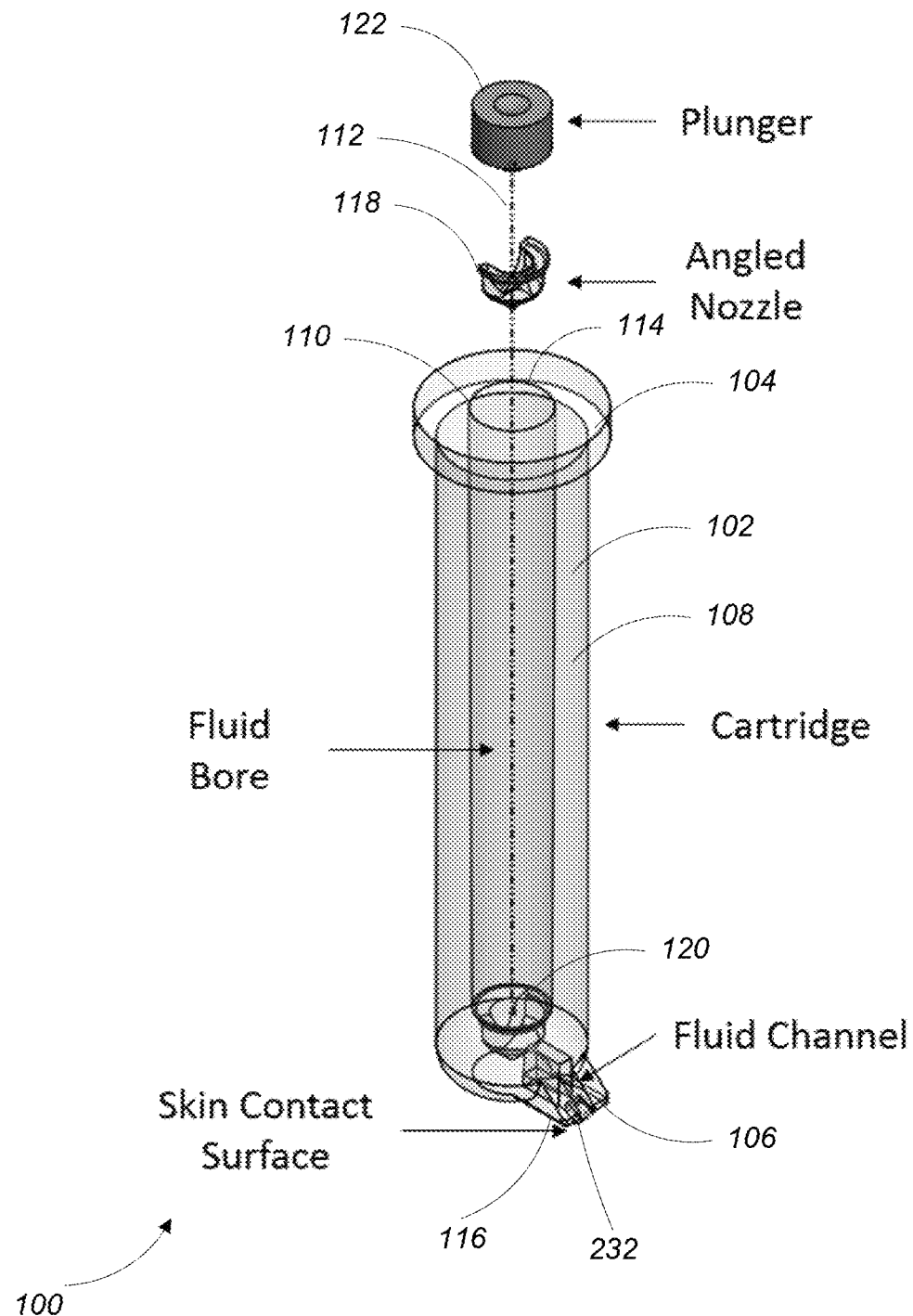
FIG. 1 is an exploded perspective view of a cartridge.

Referring to FIG. 1, a cartridge 100 for use with a needle-free transdermal injection device (not shown) includes a cartridge body 102 having a proximal end 104 and a distal end 106. The distal end 106 of the cartridge body 102 includes an injection head 116. The proximal end 104 of the cartridge body 102 includes an opening 114 which opens into a bore 110. The bore 110 is defined by a wall 108 of the cartridge body 102 and extends along a longitudinal axis 112 of the cartridge body 102.

The bore 110 is configured to receive an adapter 118, which as will be described in greater detail below includes an angled nozzle. In some examples, a distal end 120 of the bore 110 is configured to receive the adapter 118 in such a way that the adapter 118 is positioned in a predetermined orientation. In some examples, the distal end 120 of the bore 110 and the adapter are 'keyed' or have corresponding shapes that cause the adapter to be positioned in the predetermined orientation in the distal end 120 of the bore 110. In yet another example (not shown), the adapter 118 and the cartridge 100 are integrated into a single part.

The bore 110 is also configured to receive an injectate (not shown) and a plunger 122. In operation, the needle-free transdermal injection device applies a force to the plunger 122 in the bore 110 along the longitudinal axis 112 to cause the injectate in the bore 110 to be expelled from cartridge 100 via the adapter 118 and the injection head 116.

Angled Injection Features

Figure 2:
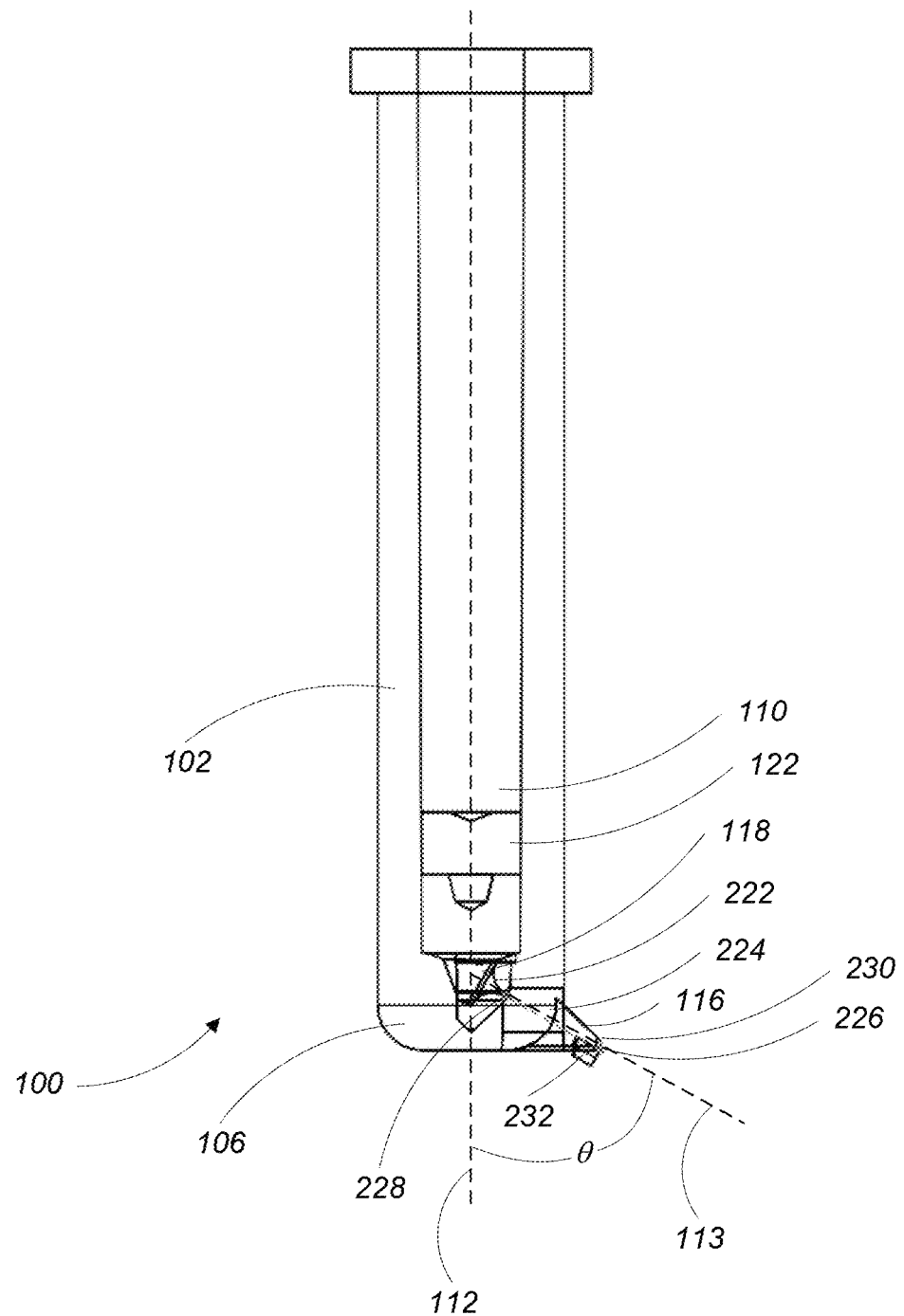
FIG. 2 is a side view of the cartridge of FIG. 1.

Referring to FIG. 2, in an assembled configuration of the cartridge 100, the adapter 118 is positioned in the predetermined orientation in the bore 110 such that a nozzle 222 of the adapter 118 points in a direction along an injection axis 113 that is angularly offset by an angle, θ from the longitudinal axis 112. The injection head 116 includes a channel 224 that extends along the injection axis 113 between an opening 228 in the bore 110 that is aligned with nozzle 222 of the adapter 118 and an injection opening 226 disposed at a distal end 230 of the injection head 116. In some examples, the distal end 230 of the injection head 116 includes a skin depressor 232 for deforming a patient's skin such that the patient's skin is substantially perpendicular to the injection axis 113 at the injection location. Further details relating to the structure for a skin depressor or surface positioned are described in Ser. No. 62/258,654, entitled, Needle-Free Injection Device, filed on Nov. 23, 2015, the contents of which are incorporated herein by reference.

In operation, as the plunger 122 moves along the longitudinal axis of the cartridge body 102, injectate is forced into the nozzle 222 of the adapter 118, causing a jet of injectate to emerge, in a direction along the injection axis 113, from the nozzle 222. The jet of injectate travels through the channel 224 of the injection head 116 and out of the injection opening 226, at which time it penetrates the patient's skin (at the angle θ relative to the longitudinal axis 112) to a predetermined depth.

Figure 3:
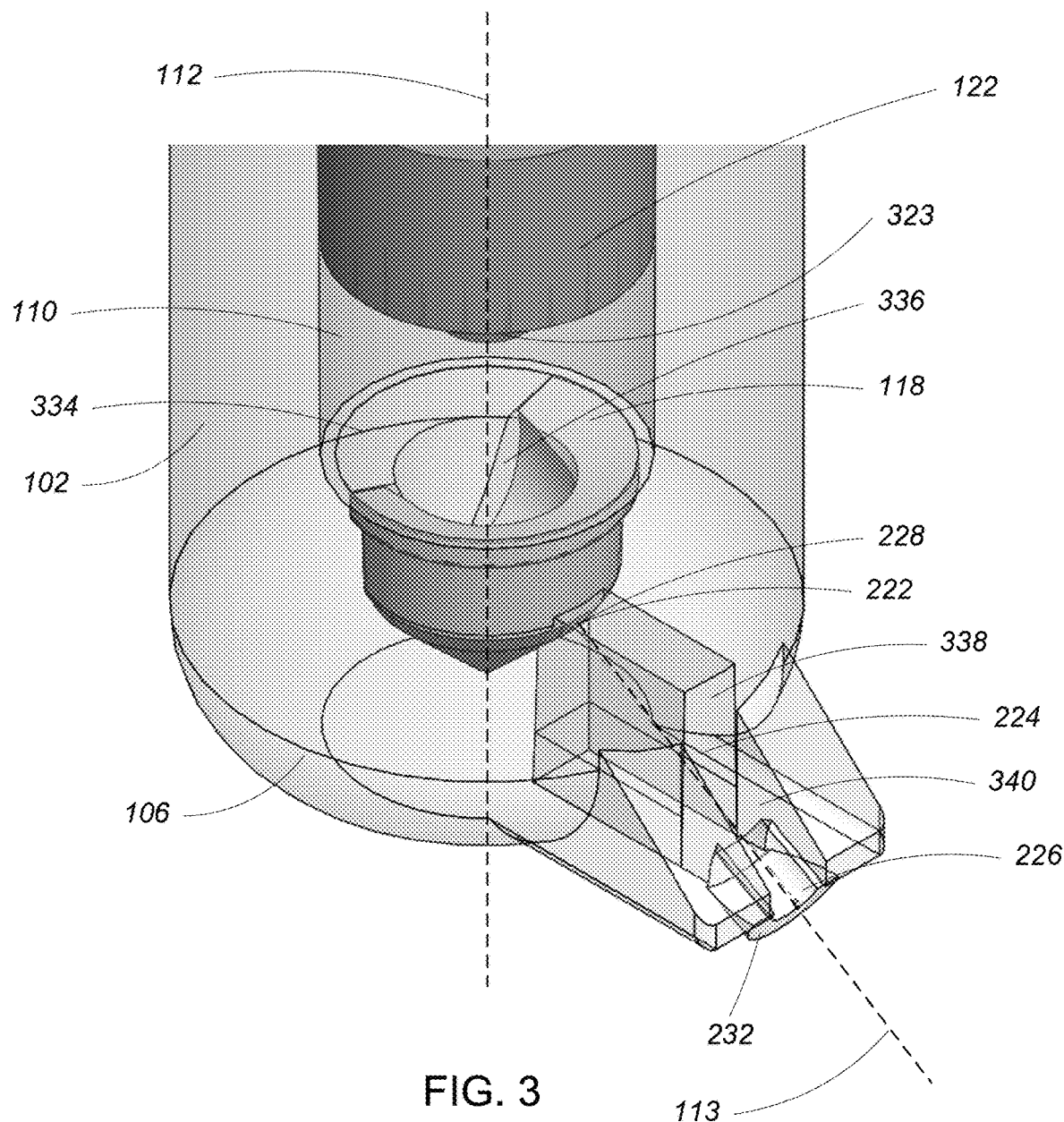
FIG. 3 is a transparent view of the distal end of the cartridge of FIG. 1.

Referring to FIG. 3, a detailed view of the distal end 106 of the cartridge body 102 shows the adapter 118 received in the predetermined orientation in the bore 110. In particular, when viewed in a direction along the longitudinal axis 112, the adapter 118 has a semicircular shape that interfaces with a corresponding semicircular key 334 of the bore 110 to ensure that the adapter 118 is positioned with the nozzle 222 aligned with the injection axis 113. With the adapter 118 received in the predetermined orientation, the semicircular key 334 of the bore 110 and the adapter 118 form a depression 336 in which injectate pools prior to ejection through the nozzle 222. In some examples, the plunger 122 includes a protrusion 323 that fits into the depression 336 to ensure that a maximum amount of injectate is expelled from the bore 110.

In some examples, the channel 224 extending from the opening 228 in the bore 110 to the injection opening 226 along the injection axis 113 extends through a rectangular cavity 338 and through an open portion 340. In other examples, the channel 224 has another shape such as a closed cylindrical or arched shape.

Adapter Configuration

Figure 4:
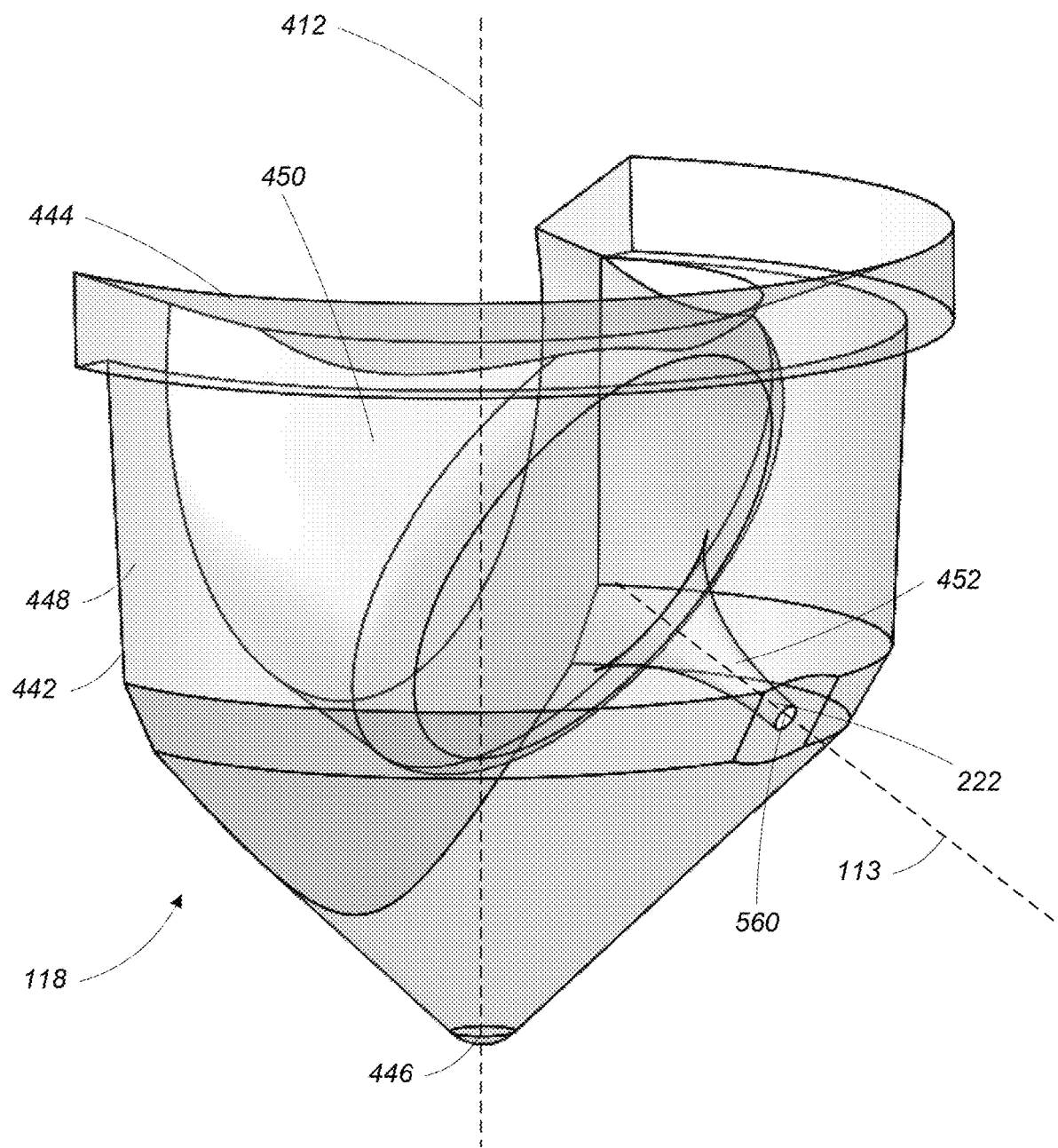
FIG. 4 is a transparent perspective view of an adapter shown in FIG. 1.

Referring to FIG. 4, the adapter 118 includes a body 442 having a first end 444, a second end 446, and a longitudinal axis 412 extending from the first end 444 to the second end 446. The body 442 includes a sidewall 448 which defines a chamber 450. The sidewall 448 has a semi-cylindrical shape such that the chamber 450 is open on one side of the body 442. It is the open side of the body 442 that has a shape configured to interface with the corresponding semicircular key 334 of the bore 110 to ensure that the adapter 118 is positioned with the nozzle 222 aligned with the injection axis 113.

The nozzle 222 forms a passageway 452 extending through the sidewall 448 and having an input in the chamber 450. As is described above, the passageway 452 of the nozzle 222 extends along an injection axis 113 that is angularly offset from the longitudinal axis 412 of the adapter 118. In some examples, the passageway 452 of the nozzle is tapered with an opening 560 of the nozzle 222 in the chamber 450 being larger than an opening of the nozzle 222 on an outer side of the sidewall 448. In some examples, the nozzle 222 has an input that is about 3.0 mm in diameter, the passageway 452 that is about 1.5 mm in length, and an output that is about 100 μm. Further details as to the configuration and specific geometry of the nozzle can be found in Ser. No. 14/788,001, entitled "Nozzle for Use in an Ultra-High Velocity Injection Device," filed on Jun. 30, 2015, the contents of which are incorporated herein by reference.

In some examples, the first end 446 of the adapter body 442 has an at least partially conical shape that corresponds to a conical recess at the distal end 120 of the bore 110.

Figure 5:
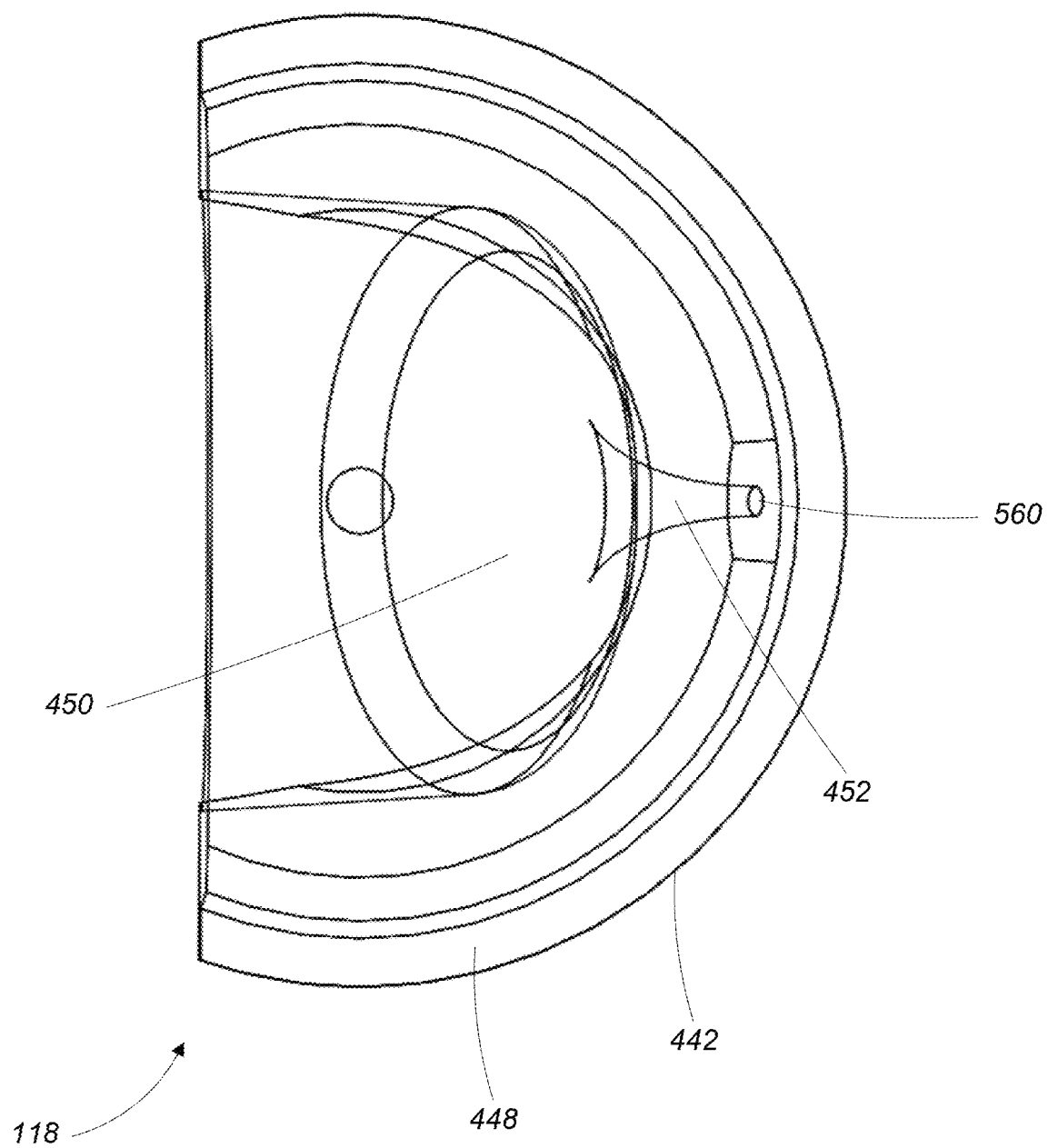
FIG. 5 is a top view of the adapter shown in FIG. 4.

Referring to FIG. 5, a shape of the sidewall 448 is semi-circular when viewed along the longitudinal axis 413 of the adapter body 442. The passageway 452 of the nozzle extends from the chamber 450 to an opening 560 on an outer surface of the sidewall 448.

It is also important to note that the structure and configuration of cartridge 100 is designed to facilitate the use of injection molding. In particular, because the cartridge may be constructed using a number of injection molded parts that have surfaces that mate with each other, the structure of those individual mating parts must be designed to permit separation of the molds used in the injection molding process. For example, the distal end 120 of the bore 110, which receives the adapter 118 is designed to allow the mating parts of the cartridge 100 to be separated while including the structural features necessary for receiving the adapter 118. Similarly, the size and shape of skin depressor 232 as well as the channel 224 including the rectangular cavity 338 of the cartridge 100 are designed to facilitate the use of injection molding the cartridge 100.

It is to be understood that the foregoing description is intended to illustrate and not to limit the scope of the invention, which is defined by the scope of the appended claims. Other embodiments are within the scope of the following claims.

What is claimed is:

1. An adapter for use with an injection device, the adapter comprising a body including:
 a first end, a second end and a first longitudinal axis extending from the first end and the second end,
 a chamber defined by a sidewall between the first end and second end,
 a nozzle having an input, an output opening, and a passageway from the input to the output opening, the passageway having an injection axis extending through the input and the output opening and to an outer surface of the body, the output opening and the injection axis being angularly offset from the first longitudinal axis of the body;
 wherein the output opening of the nozzle is spaced from an injection site during injectate delivery to the injection site, and wherein a plunger is configured to fit into a depression of the adapter in which the injectate pools prior to ejection.

2. The adapter of claim 1 wherein the passageway includes a taper, over a path length from a first dimension at the input of the nozzle to a second dimension, less than the first dimension, at the output opening of the nozzle.

3. The adapter of claim 2 wherein the first dimension and second dimension are a first diameter and a second diameter, respectively.

4. The adapter of claim 3 wherein the path length of the taper is at least 0.5 mm in length, the taper is continuous along the path length, and a diameter of the passageway monotonically decreases from the input of the nozzle to the output opening of the nozzle.

5. The adapter according to claim 3, wherein the taper of the passageway has a curve that is concave along the path length.

6. The adapter according to claim 5, wherein a tangent to the curve of the passageway is not parallel to the passageway over the path length.

7. The adapter according to claim 3, wherein a diameter at the output opening of the nozzle is less than 300 μm.

8. The adapter according to claim 3, wherein a diameter at the output opening of the nozzle is less than 100 μm.

9. The adapter according to claim 2, wherein the path length is 1.0 mm.

10. The adapter according to claim 2, wherein the shape of the taper is approximately exponential.

11. The adapter according to claim 2, wherein the taper is shaped to provide a ratio of (b) radial velocity of material at the output opening of the nozzle to (a) axial velocity of material at the output opening of the nozzle that is less than 0.50.

12. A cartridge for administering an injectate to a target underlying a contact surface, the cartridge having a distal end and comprising:
 a housing having an axis extending from a proximal end to a distal end of the housing, the housing having a bore extending along a first longitudinal axis from the proximal end to the distal end, an outer surface, and an opening at the distal end of the housing;
 an adapter disposed at the distal end of the housing, the adapter including a body having:
 a first end, a second end and a second longitudinal axis extending from the first end and the second end and substantially in parallel with the first longitudinal axis;
 a chamber defined by a sidewall between the first end and second end,
 a nozzle having a passageway, the passageway having an input at the chamber, an output opening, and an injection axis extending from the input to the output opening, the injection axis and the output opening being angularly offset from the first longitudinal axis;
 wherein the output opening of the nozzle is spaced from an injection site during injectate delivery to the injection site, and wherein a plunger is configured to fit into a depression of the adapter in which the injectate pools prior to ejection.

13. The cartridge of claim 12 further comprising an injection head disposed at the distal end of the housing.

14. The cartridge of claim 13 wherein the injection head includes a skin depressor for deforming the contact surface such that the contact surface is substantially perpendicular to the injection axis.

15. The cartridge of claim 13 wherein the injection head includes a channel extending along the injection axis from an opening in a distal end of the bore to an injection opening of the injection head.

16. The cartridge of claim 15 wherein the channel includes a first portion with a cuboid shape and a second, open portion.

17. The cartridge of claim 15 wherein the channel has a cylindrical shape.

18. The cartridge of claim 15 wherein the channel has an arched shape.

19. The cartridge of claim 12 further comprising a plunger disposed in the bore for ejection of injectate from the bore.

* * * * *